United States Patent [19]

Bayly et al.

[11] 4,115,065

[45] Sep. 19, 1978

[54] SATURATION ANALYSIS OF FOLATE COMPOUND WITH SELENIUM-75 LABELED FOLATE

[75] Inventors: Russell James Bayly; Virginia Edith May Chambers; Reginald Monks, all of Amersham, England

[73] Assignee: The Radiochemical Centre Limited, England

[21] Appl. No.: 531,748

[22] Filed: Dec. 11, 1974

[30] Foreign Application Priority Data

Dec. 11, 1973 [GB] United Kingdom ............... 57433/73

[51] Int. Cl.² .................... G01N 33/16; A61K 43/00
[52] U.S. Cl. ................. 23/230.6; 23/230 B; 424/1; 424/1.5
[58] Field of Search ............... 23/230 B, 230.3, 230.6; 424/1.5, 12

[56] References Cited

U.S. PATENT DOCUMENTS

| Re. 29,480 | 11/1977 | Axen | 23/230 B X |
| 3,505,019 | 4/1970 | Axen | 23/230.6 |
| 3,988,431 | 10/1976 | Givas | 23/230 B |
| 3,989,812 | 11/1976 | Barrett | 23/230 B X |

OTHER PUBLICATIONS

S. P. Rothenberg, Metabolism, 22 (8), 1075–1082, (Aug. 1973).
Chemical Abstracts, 77:27753z (1972).

*Primary Examiner*—Sidney Marantz
*Attorney, Agent, or Firm*—Wenderoth, Link & Ponack

[57] ABSTRACT

Folic acid and related compounds are assayed by competitive radio-assay using a selenium - 75 labelled version of folic acid as the competing compound.

2 Claims, No Drawings

SATURATION ANALYSIS OF FOLATE COMPOUND WITH SELENIUM-75 LABELED FOLATE

This invention relates to folate compounds, to the saturation analysis of folate compounds by competitive radio-assay, and to novel radioactively labelled derivatives of folate compounds.

Folic acid has the formula (I)

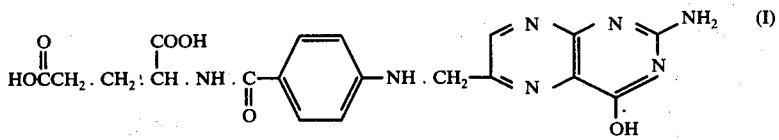

Naturally occurring folic acid is invariably in a mixture with other related compounds, and it is this naturally occurring mixture which is referred to herein as folate compounds. The other related compounds may have the formula (II)

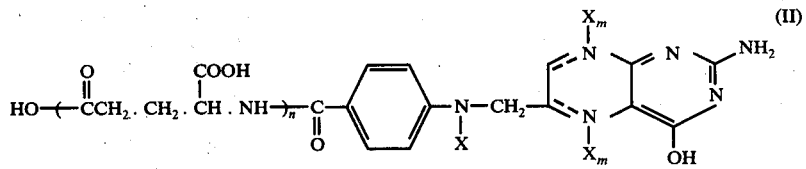

where a dotted second bond line indicates that the bond may be single or double, and where X is H, —$CH_3$, —CHO, or —$CH_2OH$ m is 0 or 1 (such that the adjacent nitrogen atom is always trivalent), and n is from 1 to 11.

Alternatively, the groups X attached to the nitrogen atoms in the 5 - and 10 - positions may be absent and replaced by a methylene bridge. The term folate compounds covers esters and salts of the above acids.

In the practice of saturation analysis using radioactive labelled compounds an essential ingredient is a labelled version of the substance to be measured which competes for binding sites in a quantitatively definable manner with the native substance, and which can readily be counted after an appropriate separation procedure. The compounds it is desired to measure are typically organic compounds present in small or very small amounts in body fluids or tissues. These compounds frequently contain at the most only the elements carbon, hydrogen, oxygen, nitrogen, phosphorus and sulphur. This introduces a severe limitation on the range of radionuclides available for labelling. C14 is the only practical isotope of carbon which can be used, and tritium the only radioactive isotope of hydrogen. Neither oxygen or nitrogen have radioactive isotopes with half-lives in excess of 10 minutes. Phosphorus and sulphur are less commonly found in the compounds of interest, but even then the only practical radionuclides are P32, a pure Beta emitter with a half-life of approximately 14 days, and S35, another pure β-emitter with a half-life of approximately 87 days. Carbon-14 is another pure β-emitter and has the additional disadvantage for many applications of a low specific activity because of its very long half-life, and tritium has only a very weak β-emission. In summary, not one of these elements has a usable γ-emitting isotope, and the β-emitters have various disadvantages.

This has led to the use of labelling with "foreign" nuclides for which the requirements are:

(i) It must have a "suitable" half-life; if too short it is impracticable to use and if too long, it will have a low specific radioactivity even when nuclidicly pure.

(ii) It should emit γ-radiation of a suitable energy. The counting of γ-emitters is more rapid and more economical than that of β-emitters.

(iii) It should be economically available at an adequate specific radioactivity.

(iv) It should be capable of stable incorporation in a range of compounds.

(v) It should produce the minimum distortion to the molecule in which it is introduced.

Virtually the only γ-emitting nuclides used in radioactive saturation analysis to date, have been the two iodine isotopes, I125 and I131. When measured against the criteria outlined above, it is apparent that the iodine isotopes are acceptable though with some limitations: the 8-day half-life of I131 is too short for many purposes and even the 60 days for I125 is sometimes undesirably short. I125 has soft γ-radiation and X-rays which can be adsorbed in a fashion which limits its ease of counting. Se75 has certain advantages over the more commonly used iodine isotope, I125. It has a longer half-life (120 days) and a more energetic γ-emission which will facilitate counting. It can be readily prepared by neutron irradiation of enriched Se74 at specific radioactivities which are adequate for many purposes; if higher specific activities are needed the bombardment of As75 with protons in a cyclotron yields essentially carrier-free Se75.

Levels of folate in samples may be determined by methods of saturation analysis employing tritiated folic acid as the radioactive ligand. The use of gamma-emitting isotopes to label the radioactive ligand would appear feasible for iodine-125 and selenium-75. Although iodine can be introduced into the p-aminobenzoate moiety of folates, the product is unsuitable for saturation analysis of folates. The radioiodinated material cannot be produced at sufficiently high specific activity and does not compete adequately with natural folates for the binding proteins used in saturation analysis of folates. Alternative approaches to introducing iodine-125 into folates involve the replacement of the L-glutamate residue of folates by a radioiodinated species such as iodotyramine-I125 or iodotyrosine-I125. This replacement may be affected by coupling either iodotyramine-I125, or iodotyrosine-I125 or one of its esters, to pteroic acid or a derivative of pteroic acid, or alternatively, by radioiodinating an inactive conjugate of pteroic acid and a moiety such as tyramine or tyrosine. Labelling of folates could also be effected by coupling either iodotyramine-I125 or iodotyrosine-I125 directly to, for example, folic acid to form pteroyl-L-glutamyl-iodotyrosine-I25.

In the case of selenium-75 labelling the possibility arises of replacing the p-aminobenzoyl moiety with a selenophene derivative or displacing a 4-tosyl group with a selenium containing nucleophile, e.g. SeCN$^-$, H Se$^-$, or CH$_3$Se$^-$. The former case would involve some intricate synthetic chemistry whilst in the latter case a determinant group in the binding of folic acid to proteins, viz. the pteridine group, would be modified. However, the introduction of selenium-75 into the folate molecule can be accomplished likewise to the introduction of iodine-125 by replacing the L-glutamate residue of folates with a selenium-75 labelled seleno-amine or seleno-amino-acid, e.g. selenomethionine-Se75, methyl-selenocysteine-Se75, or 2-(methylseleno)-ethylamine-Se75. This replacement may be affected similarly by coupling one of these seleno-amines or amino-acids to pteroic acid or a derivative of pteroic acid. Alternatively, the halogen atom of a conjugate formed from pteroic acid and a halogen-substituted amino-acid, such as β-chloroalanine or β- or γ-chloroglutamic acid, could be substituted with a selenium-75, containing nucleophile, e.g. CH$_3$Se$^-$. Labelling of folates with selenium-75 could also be effected by coupling, for example, selenomethionine-Se75 directly to folic acid to form pteroyl-L-glutamyl-selenomethionine-selenium-75.

One advantage of labelling with selenium over labelling with iodine is that modifications to the steric configuration of the folic acid molecule may be more limited. The binding of the radioactive ligand to a protein may therefore more closely resemble the binding of the natural folic acid.

The preparation of amino-acid analogues of folates for the study of enzyme systems has been previously described, e.g. in The Journal of Biological Chemistry, Volume 242, No. 7, (Apr. 10, 1967) pages 1466–76. The methods used for these syntheses are well-known in the art, consisting of the reaction of isobutyl chloroformate with a N$^{10}$-protected pteroic acid in the presence of a tertiary amine, the reaction being carried out under anhydrous conditions in dry solvents such as dioxan and dimethylformamide in order to form the mixed anhydride. The mixed anhydride is subsequently reacted with the required amino-acid ester in aqueous organic media to form an amino-acid conjugate of pteroic acid. If these reactions are applied to a range of selenium-75 labelled amines or amino-acids, e.g. selenomethionine, selenoethionine, Se-methylselenocysteine, Se-ethylselenocysteine, 2-(methylseleno)-ethylamine, then a range of selenium-75 labelled amino-acid analogues of folic acid may be prepared which can find use radioactive ligands in the saturated analysis of folates.

The present invention accordingly provides a method of performing a saturation analysis of a folate compound by causing the compound which is to be analysed and a radioactively labelled version of the said compound to compete for reaction with a binding reagent for the said compound, which is present in an amount insufficient to combine with all of said compound and and the labelled version thereof, separating the bound compound from the unbound compound and measuring the radioactive concentration of one or both of the bound and the unbound compound, characterised in that the radioactively labelled version of the folate compound is labelled with selenium-75.

The invention also provides an assay kit for performing the saturation analysis defined above, which kit comprises—

(a) a selenium-75 labelled version of the folate compound to be analysed, (b) a binding reagent to combine with the compound to be analysed, (c) preferably, a supply of a folate compound, for use in preparing standards, (d) preferably, means for separating the bound compound from the unbound compound, and (e) preferably, a plurality of tubes for performing the analysis.

The labelled version of the compound to be analysed and the binding reagent therefore may conveniently be pre-dispensed into the tubes and freeze-dried.

Thus, for example, in the case of a total serum folate assay, the kit might be supplied with vials containing the selenium-75 labelled folate derivative, β-lactoglobulin or porcine serum as binding protein, N$^5$-methyltetrahydrofolate or folate as standards and albumin — or haemoglobin-coated charcoal for separating the bound compound from the unbound compound.

Examples of systems to which saturation analysis of folates can be applied in principle include (i) the total folate content of serum (ii) the total folate content of red cells (iii) specific naturally occurring folates e.g. N$^5$-methyltetrahydrofolate and folic acid.

The following Examples illustrate the invention, Examples 1 to 3 describe the preparation of three novel selenium-75 derivatives of compounds related to folic acid. Examples 4 to 13 describe competitive radioassays of folate compounds.

EXAMPLE 1

Preparation of Se-methyl-L-selenocysteine-Se75

Sodium (24mg; 1.05 m atom) was added to a reaction vessel containing red selenium-Se75 (78.5mg; 1.0 m atom; 295mCi) suspended in 20ml of liquid ammonia, the reaction vessel being connected to a vacuum manifold and vented to the atmosphere via a Carbasorb/-charcoal trap. The reaction mixture was stirred until a red-brown solution of disodium diselenide was obtained. β-chloro-L-alanine, sodium salt (205mg; 1.41 m mol) was then added to the solution and stirring was continued until the ammonia had evaporated. The residue of crude selenocystine-Se75 was carefully dissolved in 2 molar hydrochloric acid and a precipitate of red selenium was removed by centrifugation. The pH of the supernate was adjusted to 6–7 with 4 molar ammonium hydroxide. The yellow precipitate which deposited was separated, washed with water (1 ml) and ethanol (3 ml), and dried in vacuo to yield L-selenocystine-Se75 (136mg; 0.407 m mol; 236 mCi).

L-selenocystine-Se75 (100mg; 0.3 m mol; 172 mCi) was transferred to a reaction vessel into which 20 ml of liquid ammonia was condensed. Sodium (32.9mg; 1.43 m atom) was added to the reaction vessel, and after reaction had taken place, methyl iodide (125 μl; 2 m mol) was added to the stirred solution causing the blue colouration to be discharged. After a further 10 minutes reaction ammonium iodide (164mg; 1.13 m mol) was added and the ammonia then allowed to evaporate. The residue was dissolved in water (1 ml) and reprecipitated with acetone (8 ml). The product was separated, redissolved in water (1 ml), and reprecipitated with ethanol (2 ml). After cooling the aqueous-alcoholic solution for 1 hour the product was separated by centrifugation, washed with ethanol (1 ml), and dried in vacuo to yield Se-methyl-L-selenocysteine-Se75 (29mg; 0.15 m mol; 44 mCi).

Preparation of N-Pteroyl-Se-methyl-L-selenocysteine-Se75

Isobutyl chloroformate (13.5 ul) and triethylamine (13.5 ul) were added under anhydrous conditions to $N^{10}$-trifluoroacetylpteroic acid (22 mg; vacuum dried) in dry dimethylformamide (0.5 ml) at 5° C. The mixture was allowed to react under nitrogen and attain room temperature over a period of 30 minutes in order to form the mixed anhydride. A further 2 ml of dimethylformamide was added to the reaction mixture followed by the addition of Se-methyl-L-selenocysteine-Se75, sodium salt (14 mg; 18.4 mCi) in water (1.5 ml). The reaction mixture was stirred overnight at room temperature and then left for a further 24 hours. It was then lyophilized and the residue was heated at 60° C. for 30 minutes with 0.1 molar sodium hydroxide (3 ml) in order to remove the trifluoroacetyl group; the hydrolysis was conducted in darkness under an atmosphere of nitrogen. The solution was cooled and adjusted to pH 3.0 with dilute hydrochloric acid, whereupon a precipitate formed. The precipitate was separated by centrifugation, washed with water (2 ml), and after dissolving in dilute ammonium hydroxide solution (0.25 ml of 0.05 M) was purified by thin layer chromatography (Avicel F 1 mm cellulose; Eluent: 5% aqueous ammonium bicarbonate). The chromatography was conducted in darkness. The plate was autoradiographed and the component at Rf approx. 0.19 was removed and extracted into 0.1 molar ammonium hydroxide to give 2.4 m Ci of a solution of N-Pteroyl-Se-methyl-L-selenocysteine-Se75, λ max 259, 286 nm (pH 11.0 phosphate buffer).

EXAMPLE 2

Preparation of N-Pteroyl-L-selenomethionine-Se75

Isobutyl chloroformate (13.5 μl) and triethylamine (13.5 μl) were added under anhydrous conditions to $N^{10}$-trifluoroacetylpteroic acid (22mg; vacuum dried) in dry dimethylformamide (1ml) at 5° C. The mixture was allowed to react under nitrogen and attain room temperature over a period of 30 minutes in order to form the mixed anhydride. A further 2ml of dimethylformamide was added to the reaction mixture followed by the addition of L-selenomethionine-Se75, sodium salt (3.5mg; 20mCi) in water (1ml). The reaction mixture was stirred overnight at room temperature. It was then lyophilized and the residue was heated at 60° C. for 40 minutes with 0.1 molar sodium hydroxide (3ml) in order to remove the trifluoroacetyl group; the hydrolysis was conducted in darkness under an atmosphere of nitrogen. A small yellow precipitate which formed was redissolved by the addition of 0.1 molar sodium hydroxide. The solution was cooled to approximately 5° C. and adjusted to pH 3.0 with dilute hydrochloric acid, whereupon a yellow precipitate formed. The precipitate was separated by centrifugation, washed with water (2ml) and then stirred for 10 minutes with 1.0 molar ammonium hydroxide (2ml). The remaining yellow solid was separated, washed with water (2ml), and dried in vacuo to yield 1.75mCi of N-Pteroyl-L-selenomethionine-Se75, λ max 259, 281nm (pH 11.0 phosphate buffer).

EXAMPLE 3

Preparation of 2-(methylseleno)-ethylamine-Se75

Sodium (9.2mg; 0.4 m atom) was added to a reaction vessel containing red selenium-Se75 (28.8mg; 0.366m atom; 3.8mCi) in 25ml of liquid ammonia, the reaction vessel being connected to a vacuum manifold and vented to the atmosphere via a Carbasorb/charcoal trap. The reaction mixture was stirred for approximately 10 minutes until a brown solution of disodium diselenide was obtained. Methyl iodide (65.2mg; 0.46m mol) was added to the stirred solution to give a colourless solution of dimethyl diselenide. After approximately 3 minutes a further quantity of sodium (11mg) was added to the reaction vessel until a permanent blue-black colouration was obtained, indicating complete cleavage of the diselenide bond with formation of sodium methyl selenide. 2-bromoethylamine hydrobromide (83mg; 0.4m mol) was added to the reaction mixture which was then stirred until all the ammonia had evaporated. The residue was dried in vacuo, dissolved in ethanol, and purified by preparative thin layer chromatography (Avicel F 1mm cellulose. Eluent: butanol, water, acetic acid (15:25:60) ). The plate was autoradiographed and the major component, corresponding on an analytical plate to the fastest running component with Rf 0.81, was removed and extracted into ethanol to give 1.4mCi of 2-(methylseleno)-ethylamine-Se75.

Coupling of $N^{10}$-Trifluoroacetylpteroic acid with 2-(methylseleno)-ethylamine-Se75

Isobutyl chloroformate (11 μl) and triethylamine (10 μl) were added under anhydrous conditions to $N^{10}$-trifluoroacetylpteroic acid (20mg; 0.049 m mol; vacuum dried) in dry dimethylformamide (0.4 ml) at 10° C. The solution was stirred at room temperature for 45 minutes. Further triethylamine (20 μl) was then added and the solution was transferred to a flask containing 2-(methylseleno)-ethylamine-Se75 (16mg; 0.12m mol; 1.2mCi). The reaction mixture was stirred overnight at room temperature and was then subjected to thin layer chromatography (Merck Kieselgel 60F$_{254}$. Eluent: methanol). The required product was located by autoradiography and UV fluorescence. The component at Rf 0.63 was removed and extracted into methanol to give 120 μCi of a methanolic solution of the 2-(methylseleno)-ethylamine-Se75 conjugate of $N^{10}$-Trifluoroacetylpteroic acid, λ max 257, 286 nm (pH 11.0 phosphate buffer). This product can be converted to N-pteroyl-2-(methylseleno)-ethylamine-Se75 by the hydrolysis technique generally described in Examples 1 and 2.

EXAMPLE 4

A Typical Assay for folates: using Se-75-labelled Pteroyl-L methylselenocysteine Standard solutions of $N^5$-methyltetrahydrofoate containing 0, 0.25, 0.5, 1, 2 and 4 ng in phosphate-albumin buffer (200 μl) were pipetted in assay tubes. Buffer was also added to 'total' and 'blank' tubes (400 and 300 μl respectively). To each tube was added pteroyl-L-methylselenocysteine-Se75 (0.5 ng, sp. act. ca 0.24 Ci/m.mole) in 100 μl of buffer. Immediately afterwards β-lactoglobulin (100 μg) in 100 μl of buffer was added to all tubes except the blanks. After 60 minutes incubation at room temperature, a suspension of albumin-coated charcoal in buffer (200 μl) was added at 4° C. to all tubes except the totals. The tubes were centrifuged (2000g for 10 minutes) and the supernate was counted for 300 seconds in an NE8312 beta-gamma counter.

Results are expressed in terms of $$\text{Percent bound} = 100 \times \frac{\text{Counts minus Blank count}}{\text{Total - Background}}$$

| Weight of $N^5$methyltetrahydrofolate (ng) | Percentage of labelled folate bound |
|---|---|
| 0 | 94 |
| 0.25 | 81.8 |
| 0.25 | 78.0 |
| 0.5 | 81.4 |
| 0.5 | 78.3 |
| 1 | 78.6 |
| 1 | 51.3 |
| 2 | 58.0 |
| 2 | 44.4 |
| 4 | 34.1 |

EXAMPLE 5

A Typical Assay for Folate Using Folic Acid Standards

The protocol of example 4 was used except that folic acid was used as the standard instead of $N^5$-methyltetrahydrofolate

| | Results |
|---|---|
| Weight of folic acid (ng) | percentage of labelled folate bound |
| 0 | 95.5 |
| 0.25 | 86.1 |
| 0.25 | 85.6 |
| 0.5 | 67.7 |
| 0.5 | 82.5 |
| 1 | 45.5 |
| 1 | 41.4 |
| 2 | 28.1 |
| 2 | 32.6 |
| 4 | 10.4 |

EXAMPLE 6

A typical assay for folates using Se75-labelled pteroyl-L-selenomethionine

The protocol of example 4 was used except that Se75-pteroyl-L-selenomethionine (0.5ng, sp. act. ca 2.25 Ci/m.mole) was substituted as label for Se75-pteroyl-L-methylselenocysteine.

| | Results |
|---|---|
| Weight of $N^5$methyltetrahydrofolate (ng) | Percent of labelled folate bound |
| 0 | 49.9 |
| 0.25 | 39.3 |
| 0.25 | 36.1 |
| 0.5 | 35.9 |
| 0.5 | 37.3 |
| 1 | 32.6 |
| 1 | 33.0 |
| 2 | 25.9 |
| 2 | 25.4 |
| 4 | 24.1 |

EXAMPLE 7

The protocol of example 6 was used except that a solution of porcine serum (30 μl) in buffer (70 μl) was substituted for β-lactoglobulin as binding protein.

| | Results |
|---|---|
| Weight of $N^5$methyltetrahydrofolate (mg) | Percent of labelled folate bound |
| 0 | 36.4 |
| 0.25 | 21.3 |
| 0.5 | 17.2 |
| 0.5 | 17.1 |
| 1 | 20.7 |
| 1 | 18.5 |
| 2 | 19.3 |
| 2 | 17.2 |
| 4 | 15.5 |
| 4 | 15.6 |

EXAMPLE 8

The protocol of example 4 was used except that a solution (100 μl) containing 30 μl of porcine serum and 70 μl of buffer was used instead of β-lactoglobulin as binding protein.

| | Results |
|---|---|
| Weight of $N^5$methyltetrahydrofolate (ng) | Percent of labelled folate bound |
| 0 | 89.3 |
| 0.25 | 61.4 |
| 0.25 | 52.0 |
| 0.5 | 43.3 |
| 0.5 | 48.1 |
| 1 | 41.2 |
| 1 | 38.9 |
| 2 | 40.9 |
| 2 | 39.3 |
| 4 | 34.5 |
| 4 | 31.0 |

EXAMPLE 9

The protocol of example 8 was used except that folic acid was substituted for $N^5$-methyltetrahydrofolate as standard

| | Results |
|---|---|
| Weight of folic acid (ng) | Percent of labelled folic acid bound to porcine serum |
| 0 | 92.7 |
| 0.25 | 67.1 |
| 0.25 | 68.7 |
| 0.5 | 60.9 |
| 0.5 | 43 |
| 1 | 26.2 |
| 1 | 31.3 |
| 2 | 28.0 |
| 2 | 28.3 |
| 4 | 9 |
| 4 | 2.6 |

EXAMPLE 10

The protocol of example 6 was used except that folic acid was substituted for $N^5$-methyltetrahydrofolate as standard.

| | Results |
|---|---|
| Weight of folic acid (ng) | Percent of labelled folate bound |
| 0 | 59.1 |
| 0.25 | 38.1 |
| 0.25 | 37.2 |
| 0.5 | 34 |
| 0.5 | 30.7 |
| 1 | 19 |
| 1 | 22.6 |
| 2 | 14.2 |
| 2 | 13.2 |
| 4 | 5.8 |

-continued

| Results | |
|---|---|
| Weight of folic acid (ng) | Percent of labelled folate bound |
| 4 | 8 |

EXAMPLE 11

The protocol of example 10 was used except that a solution containing 30 μl of porcine serum and 70 μl of buffer was substituted for β-lactoglobulin as binding protein.

| Results | |
|---|---|
| Weight of folic acid (ng) | Percent of labelled folate bound |
| 0 | 35.7 |
| 0.25 | 20.3 |
| 0.25 | 21.1 |
| 0.5 | 18.4 |
| 0.5 | 20.9 |
| 1 | 16.8 |
| 1 | 17.3 |
| 2 | 13.0 |
| 2 | 13.9 |
| 4 | 12.6 |
| 4 | 15.2 |

EXAMPLE 12

A Typical Radioimmunoassay for folic acid using Se75-labelled Pteroyl-L-methylselenocysteine Standard solutions of folic acid containing 0, 0.25, 0.5, 1, 2 and 4 ng in phosphate-albumin buffer (200 μl) were pipetted into assay tubes. Buffer was also added to 'total' and 'blank' tubes (400 and 300 μl respectively). To each tube was added Se75-pteroyl-L-methylselenocysteine (0.5 ng, sp. act. ca 0.24 Ci/m.mole) in 100 μl of buffer. Immediately afterwards was added, to all tubes except the blanks, 100 μl of buffer containing 2 μl of a 1/15000 titre rabbit anti folic acid antiserum, raised against a conjugate of folic acid with serum albumin.

After 60 minutes incubation at room temperature, a suspension of albumin-coated charcoal in buffer (200 μl) was added at 4° C. to all tubes except the totals. The tubes were centrifuged (2000g for 10 minutes) and the supernate was counted for 300 seconds.

| Results | |
|---|---|
| Weight of folic acid (ng) | Percent of labelled folate bound to antiserum |
| 0 | 97.6 |
| 0.25 | 72.4 |
| 0.25 | 90.9 |
| 0.5 | 52.5 |
| 0.5 | 70.3 |
| 1 | 50.1 |
| 1 | 35.3 |
| 2 | 20.1 |
| 2 | 29.6 |
| 4 | 20.1 |
| 4 | 12.8 |

EXAMPLE 13

A Typical Radioimmunoassay for Folic Acid using Se-75-labelled pteroyl-L-selenomethionine The protocol of example 12 was used except that Se75-pteroyl-L-selenomethionine (0.5ng, sp. act. ca 2.25 Ci/m.mole) was substituted for Se-75-pteroyl-L-methylselenocysteine as label

| Results | |
|---|---|
| Weight of folic acid (ng) | Percent of labelled folate bound |
| 0 | 42.2 |
| 0.25 | 25.7 |
| 0.25 | 27.6 |
| 0.5 | 22.1 |
| 0.5 | 19 |
| 1 | 20.8 |
| 1 | 21.9 |
| 2 | 16.7 |
| 2 | 15.5 |
| 4 | 16 |
| 4 | 13.7 |

We claim:

1. A method of performing a saturation analysis of a folate compound by causing the compound which is to be analysed and a radioactively labelled version of the said compound to compete for reaction with a binding reagent for the said compound, which is present in an amount insufficient to combine with all of said compounds and the labelled version thereof, separating the bound compound from the unbound compound and measuring the radioactive concentration of one or both of the bound and the unbound compound, wherein the improvement comprises selecting a selenium-75 labeled version of said folate to compete for reaction with said binding reagent.

2. A method as claimed in claim 1, performed as a competitive protein binding assay in which the folate compound is folic acid and the binding reagent is β-lactoglobulin.